United States Patent
Brocart et al.

(10) Patent No.: US 11,788,137 B2
(45) Date of Patent: Oct. 17, 2023

(54) DIAGNOSTIC AND/OR SEQUENCING METHOD AND KIT

(71) Applicant: Diagenode S.A., Seraing (BE)

(72) Inventors: Gilles Brocart, Esneux (BE); Céline Sabatel, Villers-le-Temple (BE); Florence Durieux, Vivegnis (BE)

(73) Assignee: DIAGENODE S.A., Seraing (BE)

( * ) Notice: Subject to any disclaimer, the term of this patent is extended or adjusted under 35 U.S.C. 154(b) by 218 days.

(21) Appl. No.: 17/039,126

(22) Filed: Sep. 30, 2020

(65) Prior Publication Data

US 2021/0095339 A1    Apr. 1, 2021

(30) Foreign Application Priority Data

Sep. 30, 2019  (EP) .................................. 19200360
Nov. 28, 2019  (EP) .................................. 19212070

(51) Int. Cl.
*C12Q 1/6874*  (2018.01)

(52) U.S. Cl.
CPC .................................. *C12Q 1/6874* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |
| 9,765,391 B2* | 9/2017 | Swerdlow | C12Q 1/6869 |

FOREIGN PATENT DOCUMENTS

| | | |
|---|---|---|
| CN | 106757380 A | 5/2017 |
| CN | 107385516 A | 11/2017 |
| CN | 109504770 B | 11/2019 |
| WO | 2000018957 A1 | 4/2000 |
| WO | 2005065814 A1 | 7/2005 |
| WO | 2006064199 A1 | 6/2006 |
| WO | 2007010251 A2 | 1/2007 |
| WO | 2015089333 A1 | 6/2015 |
| WO | 2015106941 A1 | 7/2015 |
| WO | 2015173402 A1 | 11/2015 |
| WO | 2016048994 A2 | 3/2016 |
| WO | 2017117440 A1 | 7/2017 |
| WO | 2018035170 A1 | 2/2018 |
| WO | 2019061199 A1 | 4/2019 |

OTHER PUBLICATIONS

Macosko et al., "Highly Parallel Genome-wide Expression Profiling of Individual Cells Using Nanoliter Droplets," Cell 2015, 161: 1202-1214, with 31 pages of Supplemental Information. (Year: 2015).*
Turchinovich et al., "Capture and Amplification by Tailing and Switching (CATS)," RNA Biol. 2014, 11:817-828. (Year: 2014).*
Extended European Search Report dated May 27, 2020 in European Application No. EP19212070.7 (13 pages).
Matz, M. et al., "Amplification of cDNA ends based on template-switching effect and step-out PCR," Nucleic Acids Research, 1999, vol. 27, No. 26 (3 pages).
Extended European Search Report dated Feb. 24, 2021 in corresponding European Application No. 20199382.1 (15 pages).

* cited by examiner

*Primary Examiner* — Kaijiang Zhang
(74) *Attorney, Agent, or Firm* — Alston & Bird LLP; Jeff Landes

(57) ABSTRACT

The present invention is related to a Template Switch Oligo construct and its use into a ligase free diagnostic and/or sequencing method and to the kit for performing the method of the invention.

17 Claims, 4 Drawing Sheets

Specification includes a Sequence Listing.

SEQUENCE LISTING

<160> NUMBER OF SEQ ID NOS: 9

<210> SEQ ID NO 1
<211> LENGTH: 42
<212> TYPE: DNA
<213> ORGANISM: Artificial sequence
<220> FEATURE:

```
<223> OTHER INFORMATION: Synthetic construct
<220> FEATURE:
<221> NAME/KEY: modified_base
<222> LOCATION: (27)..(39)
<223> OTHER INFORMATION: n is a, c, g, or t
<220> FEATURE:
<221> NAME/KEY: misc_feature
<222> LOCATION: (27)..(39)
<223> OTHER INFORMATION: n is a, c, g, t or u

<400> SEQUENCE: 1
gttcagagtt ctacagtccg acgatcnnnn nnnnnnnng gg                                42

<210> SEQ ID NO 2
<211> LENGTH: 42
<212> TYPE: DNA
<213> ORGANISM: Artificial sequence
<220> FEATURE:
<223> OTHER INFORMATION: Synthetic construct
<220> FEATURE:
<221> NAME/KEY: modified_base
<222> LOCATION: (27)..(39)
<223> OTHER INFORMATION: n is a, c, g, or t
<220> FEATURE:
<221> NAME/KEY: misc_feature
<222> LOCATION: (27)..(39)
<223> OTHER INFORMATION: n is a, c, g, t or u

<400> SEQUENCE: 2
ttccctacac gacgctcttc cgatctnnnn nnnnnnnng gg                                42

<210> SEQ ID NO 3
<211> LENGTH: 42
<212> TYPE: DNA
<213> ORGANISM: Artificial sequence
<220> FEATURE:
<223> OTHER INFORMATION: Synthetic construct
<220> FEATURE:
<221> NAME/KEY: modified_base
<222> LOCATION: (27)..(39)
<223> OTHER INFORMATION: n is a, c, g, or t
<220> FEATURE:
<221> NAME/KEY: misc_feature
<222> LOCATION: (27)..(39)
<223> OTHER INFORMATION: n is a, c, g, t or u

<400> SEQUENCE: 3
gaacgacatg gctacgatcc gatcttnnnn nnnnnnnng gg                                42

<210> SEQ ID NO 4
<211> LENGTH: 20
<212> TYPE: DNA
<213> ORGANISM: Artificial sequence
<220> FEATURE:
<223> OTHER INFORMATION: Primer sequence Illumina P5

<400> SEQUENCE: 4
aatgatacgg cgaccaccga                                                        20

<210> SEQ ID NO 5
<211> LENGTH: 24
<212> TYPE: DNA
<213> ORGANISM: Artificial sequence
<220> FEATURE:
<223> OTHER INFORMATION: Primer sequence Illumina P7

<400> SEQUENCE: 5
caagcagaag acggcatacg agat                                                   24
```

```
<210> SEQ ID NO 6
<211> LENGTH: 55
<212> TYPE: DNA
<213> ORGANISM: Artificial sequence
<220> FEATURE:
<223> OTHER INFORMATION: Illumina P5

<400> SEQUENCE: 6
aatgatacgg cgaccaccga gatctacacg ttcagagttc tacagtccga cgatc         55

<210> SEQ ID NO 7
<211> LENGTH: 57
<212> TYPE: DNA
<213> ORGANISM: Artificial sequence
<220> FEATURE:
<223> OTHER INFORMATION: Illumina P7

<400> SEQUENCE: 7
gatcggaaga gcacacgtct gaactccagt cacatctcgt atgccgtctt ctgcttg       57

<210> SEQ ID NO 8
<211> LENGTH: 62
<212> TYPE: DNA
<213> ORGANISM: Artificial sequence
<220> FEATURE:
<223> OTHER INFORMATION: Illumina Dual P5

<400> SEQUENCE: 8
aatgatacgg cgaccaccga gatctacaca cactctttcc ctacacgacg ctcttccgat    60
ct                                                                   62

<210> SEQ ID NO 9
<211> LENGTH: 57
<212> TYPE: DNA
<213> ORGANISM: Artificial sequence
<220> FEATURE:
<223> OTHER INFORMATION: Illumina dual P7

<400> SEQUENCE: 9
gatcggaaga gcacacgtct gaactccagt cacatctcgt atgccgtctt ctgcttg       57
```

DIAGNOSTIC AND/OR SEQUENCING METHOD AND KIT

CROSS REFERENCE TO RELATED APPLICATIONS

This application claims the benefit under 35 U.S.C. § 119 of European Patent Application No. 19212070.7, filed Nov. 28, 2019, and European Patent Application No. 19200360.6, filed Sep. 30, 2019, both of which are incorporated herein by reference in their entireties.

FIELD OF THE INVENTION

The present invention is in the field of diagnostic and/or sequencing technologies and is related to a Template Switch Oligo construct and its use into an improved ligase free diagnostic and/or sequencing method based upon Capture and Amplification by Switching technology, especially the so-called "Capture and Amplification by Tailing and Switching" (CATS) technology. The present invention is also related to a diagnostic and/or sequencing kit comprising tools for performing the method of the invention.

SEQUENCE LISTING

This application contains a sequence listing. The sequence listing file in ASCII text format is named Sequence_Listing_150089_ST25.txt, is 2.42 KB in size, was created on Sep. 30, 2020, and is incorporated herein by reference in its entirety.

BACKGROUND OF THE INVENTION

Sequencing methods with Capture and Amplification by Switching, especially the so called "Capture and Amplification by Tailing and Switching" (CATS) technology are ligase-free methods to produce DNA libraries for a further sequencing from low amounts (about 10 pg or more) of RNA or DNA sequences and is described in the international patent application WO2015/173402-A1.

These methods are more efficient for RNA-seq library creation than protocols using ligase by incorporating adaptors during cDNA synthesis in a single reaction tube.

In particular, these methods allows optimal sequencing of a great variety of RNA species, including sensitive, degraded, cell free RNA (cfRNAs), plasma derived RNA, non-coding RNA (ncRNA), such as miRNA or long non-coding RNA (lncRNA), exosomal RNA, rare and low input RNA sample, that are efficient markers of different diseases, such as cancers.

In addition, these rapid and easy single tube methods will minimize hands-on time, reduce possible risks of contamination and are more robust against bias factors, such as RNA modifications or secondary structure that could cause preferential enrichment, than ligation based methods.

Although the CATS library preparation technology holds significant advantages, it still presents a major limitation in its sequencing ability on ILLUMINA (ILMN)® platforms. This limitation essentially comes from the fact that the ILLUMINA platforms read1 is starting by the template switch motif, a sequence motif of 3 to 5 positions, highly enriched in Guanosine (G).

Furthermore, the addition of at least 5 consecutive nucleotides (Poly-A tail) to the 3-terminus of the native (single stranded or double stranded) nucleic acid sequence or its fragments of the sample to be analyzed will generate technical problems, such as a difficult trimming and a loss of terminal As, during the data analysis of the reads generated.

Next Generation Sequencing (NGS) platforms like Illumina's are deciphering unknown sequence of DNA based on a Sequencing By Synthesis (SBS) principle. This principle is relying on the synthesis of a short piece of complementary DNA called a read that is sequentially detected by fluorimetry. The fluorimetric detection is possible thanks to labelled nucleotides that end up constituting the building blocks of the so called read.

In order to calibrate the different settings important for the read synthesis and the sequential detection of the nucleotides added, thus constituting the growing read, the sequencer uses the first sequencing cycles to map the location of the clusters, preferably in non-patterned flow cells at least, test image acquisition, balance the different fluorescent signals emitted by the different growing reads in the different clusters. This critical timeframe for the sequencing run is often called the template generation.

Once the template generation is completed, it is impossible for the sequencer to change its set parameters which will have a predominant impact on the rest of the sequencing run and on the quantity and quality of the data generated.

The template generation requires an even distribution of the four different bases (A, T, C and G) called at the same time across the flow cell during a sequencing cycle. Therefore, this library that is under the process of sequencing, must present a diverse distribution of the bases inside its sequence and across the different DNA fragments that will later on constitute the clusters on the flow cell. This is especially true for the first ten cycles of sequencing.

To this day, the small RNA-seq library preparation methods employing the template-switch to attach an Illumina adapter to the growing construct have been causing troubles in sequencing.

This is because the nature of the template switch construct contradicts directly the prerequisites of a library that will make a successful template generation on a (Illumina) sequencer.

Practically speaking, the 3 to 5 first sequencing cycles that are reading the template switch are highly unbalanced, and calling a high percentage (>60%) of the same base (G) for almost every clusters on the flow cell.

This severe lack of base diversity is causing important drawbacks in the sequencing output, especially numbers of reads generated in the end and the overall read quality.

STATE OF THE ART

The international patent application WO2018/035170 discloses in the example 2 the preparation of a sequences library for the detection of sequence variants. In a variation of the disclosed procedure of example 2, Illumina adapters are used in library preparation instead of Nextera preparation.

Table 5 of WO2018/035170 provides and the sequence SEQ. ID. NO:108 of WO2015/089333 provide examples of primers that are useful in the applied method, in particular the specific primer sequence PTEN-BX6a that includes a specific sequence composed of the Illumina P5 adaptor sequence bound by a linker sequence of 12 nucleotides to a oligonucleotide sequence and 7 additional nucleotides fixed at its 3' end.

The Chinese patent applications CN106757380 and CN107385516 disclose a primer sequence including the Illumina P5 adaptor sequence by a linker sequence of 12 nucleotides to a oligonucleotide sequence and 3 additional nucleotides at the 3' end.

The Chinese patent application CN109504770 discloses a primer sequence including the Illumina P5 adaptor sequence by a linker of 12 nucleotides to a oligonucleotide sequence and 2 additional nucleotides at the 5' end and at the 3' end.

The international patent application WO2017/117440 discloses a primer sequence including a Nextera adaptor sequence bound to a linker of 12 nucleotides to a oligonucleotide sequence and 7 additional nucleotides at the 5' end

AIMS OF THE INVENTION

The present invention aims to provide new tools and a new ligase-free sequencing method, based upon the "Capture and Amplification by Switching technology" method, preferably the "Capture and Amplification by Tailing and Switching" (CATS) method above described, that does not present the drawbacks of the method and kit of the state of the art.

A first aim of the present invention is to obtain such method and tools for performing this method, that improve the nucleic acids libraries production and sequencing, especially an increase in positive reads of sensitive, degraded, chemically modified, cell free nucleic acid sequences, especially RNA sequences, possibly obtained from a single cell and therefore having a higher diversity of the detected and sequenced nucleic acids, possibly involved in specific biological pathways and that could be factors of syndromes or diseases (such as inflammation or cancer) affecting bacteria, fungi, animal and plants cells, tissues, organs or species.

Another aim of the invention is to obtain such method and tools for performing this method, that are easy to use, with minimal hands-on time; that are also robust and present an improved sensitivity and excellent reproducibility.

SUMMARY OF THE INVENTION

To overcome this major limitation of template switch-based library preparation, the inventors have designed a new library construct using CATS technology, but wherein the Template Switching Oligonucleotide (template switch oligo, or TSO) construct, used according to the invention, contains three distinct parts, each one serving a particular function.

Therefore, a first aspect of the present invention is related to a new Template Switching Oligonucleotide (TSO) construct, also called hereafter the "improved CATS construct according to the invention", having a total length preferably comprised between 20 and 50 nucleotides, more preferably between 29 and 48 nucleotides, and comprising from the 5' end towards the 3' end, at least:
- a primer sequence, having a length preferably comprising between 10 and 40 nucleotides, more preferably comprised between 18 and 32 nucleotides, this primer preferably being part of the ILLUMINA® P5 adaptor sequence, necessary for genetic material amplification, preferably for PCR amplification, flow cell clustering and sequencing primer for read one hybridization, and
- a template switch motif sequence, having a length preferably comprised between 1 and 6 nucleotides, more preferably between 3 and 5 nucleotides, this template switch motif sequence being present in this TSO construct, and designed to match the overhang nucleotides added by the reverse transcriptase at the 3' end of a cDNA after first strand synthesis, wherein this template switch motif sequence is linked to this primer sequence by a random linker sequence of at least 6 bases, preferably between (about) 8 bases and (about) 12 bases, that will constitute the first 8 cycles to 12 cycles of the sequencing.

Preferably, in the template switch oligo (TSO) construct according to the invention, the primer sequence is further linked by its 5' end to a blocker made of a chemical blocking group, preferably selected from the group consisting of a biotin, a 5'-end abasic site (/dSp/BioSg), a 5'-end spacer (C3, C6, C9) or a 5'-end monophosphate Advantageously, the random linker sequence of the construct according to the invention comprises (about) 10, 11, 12, 13 or 14 nucleotides and is preferably composed of a more or less equal distribution of the bases A, T, C and G, i.e. from (about) 20% to (about) 30% of each base A, T, C and G (the total being 100% with the four bases), that is designed to circumvent the limitations of the template switch-based library preparation in the template generation phase.

Ultimately, since the random linker sequence present in the construct according to the invention is added to every library fragment before genetic (PCR) amplification, it can also be advantageously used as a Unique Molecular Identifier (UMI) during data analysis to eliminate PCR duplicates of a read.

Preferably, the construct according to the invention is selected from the group consisting of the sequence SEQ. ID. NO:1, the sequence SEQ. ID. NO:2, or the sequence SEQ. ID. NO:3, comprising a random linker sequence of 12 nucleotides having the sequence: NNNNNNNNNNNN but also less or more nucleotides.—wherein N is any nucleotide that comprises a base selected from the group consisting of Adenosine (A), Thymidine (T), Guanine (G) or Cytosine (C)

wherein the random linker sequence comprises more or less about 25% of each base A, T, C and G, except for certain key positions where A is omitted However in this random sequence of 12 nucleotides, several nucleotides are random, but should preferably not include the Adenosine (A) base and/or not include the Cytosine (C) base. In this random sequence of 12 nucleotides, starting from the 5' end, the $5^{th}$, possibly the $6^{th}$, the $10^{th}$, the $11^{th}$ and the $12^{th}$ nucleotides do not comprise an Adenosine (A) base. Alternatively, in this random sequence of 8 nucleotides starting from the 5' end, the $5^{th}$ and possibly the $6^{th}$ nucleotide(s) do(es) not comprise an Adenosine (A) base and the $7^{th}$ and the $8^{th}$ nucleotides do not comprise a cytosine (C) base. Furthermore in this random sequence of 10 nucleotides, starting from the 5' end; the $5^{th}$, possibly the $6^{th}$, the $7^{th}$, the $8^{th}$ nucleotides do not comprise Adenosine (A) base and the $9^{th}$ and the $10^{th}$ nucleotides do not comprise a cytosine (C) base, and wherein the sequence rNrGrGrG is the consensus template switch oligo sequence, rN is a nucleoside or any ribonucleotide of a RNA sequence, and rG is a specific nucleoside: a ribonucleotide of the base guanine (G).

Advantageously, the TSO construct of the invention is, the sequence SEQ. ID. NO:1 comprises or preferably consist of the following sequence:

5' (biotin)-

GTTCAGAGTTCTACAGTCCGACGATCNNNNNNNNNNNNrNrGrGrG-3', the sequence SEQ. ID. NO:2 comprises or preferably consists of the following sequence:

```
5' (biotin)-
TTCCCTACACGACGCTCTTCCGATCTNNNNNNNNNNNNNrNrGrG 3'
``` wherein the both sequences correspond respectively to the construct according to the invention, wherein the primer sequence is present in the known Illumina® adaptor sequence with dual indexing (CATS-ILMN (Truseq HT) and without dual indexing (CATS-IMN) (truSeqsm RNA)) and, the sequence SEQ. ID. NO:3 comprises or preferably consists of the following sequence:

```
5'(biotin)-
GAACGACATGGCTACGATCCGATCTTNNNNNNNNNNNNNrNrGrG-3'
``` is the construct according to the invention, wherein the primer sequence is present in the known MGI® adaptor sequence (CATS-MGI).

Preferably, one or more of the sequences SEQ. ID. NO:1, SEQ. ID. NO:2, and/or SEQ. ID. NO:3 is (are) also linked by the 5' end of the primer sequence to a specific chemical label group, selected from the group consisting of a biotin or a 5'-end abasic site As above mentioned, due to technical constraints arising during library preparation, certain key positions in the random linker sequence can be defined by missing intentionally 1 of the 4 bases (A, T, C or G) in the template switch oligonucleotide;

For preferred elimination and digestion purpose, it is also conceivable that the template switch oligonucleotide bears, at certain key positions, a/ideoxyU/base that will be excised after reverse transcription by a cocktail of enzymes, called the USER (and are preferably selected from the group consisting of Uracil DNA glycosylase (UDG) and the DNA glycosylase-lyase Endonuclease VIII or Antarctic Thermolabile Uracil DNA glycosylase (UDG) and the Endonuclease III)

For cleavage and elimination purpose, it is also possible that the template switch oligonucleotide contains, at certain key positions, RNA bases that are responding to an RNase H mediated digestion of the second cDNA strand of the library construct.

The unique design of this template switch oligo allows removing the barriers caused by the direct sequencing of the template switch motif in small RNA-seq applications using a template switch-based library preparation. Using this unique design of the new construct according to the invention, one might expect to have a sequencing run falling completely into ILLUMINA® specifications without using more than 1% phiX spiked-in which hasn't been possible by the past in the previously stated conditions (direct sequencing of the template switch motif).

The present invention is also related to a diagnostic and/or sequencing method, preferably high throughput diagnostic and/or sequencing method and possibly to a computer-implemented method performed under the control of processor executing instructions, which is a diagnostic and/or sequencing method of a nucleic acid strand sequence as well as tools, preferably included into a kit, for performing this method, this sequencing method comprising at least (or is consisting of) the steps of, preferably the following consecutive steps of:

providing a sample, especially liquid or solid biopsies, such as a blood sample, preferably the serum or plasma, a tissue sample, a fossil, a single cell sample or even targeted compartments of cells, such as the nucleus, the endoplasmic reticulum, . . . , this sample comprising a native single stranded nucleic acid sequence or native double stranded nucleic acid sequence, possibly fragmenting the native single stranded nucleic acid sequence or native double stranded nucleic acid sequence, into smaller nucleic acid sequence fragments, possibly denaturing the native double strand nucleic acid sequence(s), possibly end-repairing the native nucleic acid sequences, preferably adding at least 5, preferably at least 10, at least 15, at least 20, at least 25, at least 30, at least 35, but preferably less than 100, less than 75, less than 50 consecutive nucleotides to the 3' terminus of the native single stranded or native double stranded nucleic acid sequence or their fragments, preferably a poly(A) sequence, hybridizing a priming oligonucleotide sequence complementary to the added nucleotide sequence and synthesizing a cDNA sequence with a template dependent DNA polymerase to obtain a double stranded nucleic acid sequence, hybridizing to the generated double stranded nucleic acid sequence, a template switching motif sequence of a Template Switching Oligonucleotide (TSO), this template switching motif sequence being further linked in 3' to an at least 6 bases random sequence, preferably a random sequence comprised between (about) 8 bases and (about) 50 bases, preferably to 12 bases, the template switching motif sequence preferably being the Template Switching Oligonucleotide sequence of the invention, and wherein the Template Switching Oligonucleotide (TSO) will hybridize to overhang (untemplated C) nucleotides added by a reverse transcriptase during reverse transcription, extending the 3' end of the cDNA strand to synthesize a double stranded nucleic acid sequence, wherein one strand of the nucleic acid sequence comprises the priming oligonucleotide and a cDNA sequence that is complementary to the single stranded nucleic acid sequence and to the Template Switching Oligonucleotide sequence. When the reverse transcriptase reaches the 5' end of the nucleic acid sequence, it switches the template and continues DNA synthesis over the Template Switching Oligonucleotide (TSO); the Template Switching Oligonucleotide containing at least three, preferably four 3' terminal ribonucleotides x (rX) facilitates the template switching and carries the adaptor sequence, performing genetic amplification steps, preferably PCR amplification steps, when the applied method is performed upon the MGI platform with MGI tools to obtain nanoballs, possibly adding a splint oligo sequence that hybridizes to adapter DNA sequences which are ligated to form a circle and adding an exonuclease to remove all remaining single stranded and double stranded DNA products to collect only circular DNA template, performing a base sequencing, and obtaining by nanopore sequencing or imaging an identification of each nucleotide of the native nucleic acid sequence, preferably upon a high resolution CCD camera.

In the method of the invention, the synthesized double stranded nucleic acid sequences present a length preferably comprised between (about) 150 nucleotides and (about) 600 nucleotides, more preferably between (about) 200 nucleotides and (about) 500 nucleotides.

According to the invention, the native single stranded nucleic acid sequence or native double stranded nucleic acid sequence is selected from the group consisting of normal DNA or RNA sequences, fragmented and/or bisulfite-converted DNA sequence, mRNA sequence, miRNA sequence, small RNA sequence, piRNA sequence, bisulfite-converted RNA or a mixture thereof.

In the method according to the invention, these at least 5, 10, 15, 20, 25, 30, 35 consecutive identical nucleotides, are preferably selected from the group consisting of ribonucleotides, desoxy-ribonucleotides or didesoxy-ribonucleotides of A, T, C, G or U, and these nucleotides are preferably added by an enzyme, this enzyme being selected from the group consisting of a poly(A)-polymerase, poly(U)-polymerase, poly(G)-polymerase, terminal transferase, DNA ligase, RNA ligase and the dinucleotides and the trinucleotides RNA ligases.

Preferably, the method of the invention, when applied upon MGI platform with MGI tools to obtain nanoballs, is also advantageously improved prior to base sequencing step, by the addition of the step of:

obtaining DNA clusters or nanoballs (DNBs), preferably by performing a rolling circle replication of the synthesized stranded nucleic acid sequence and fixing the DNA clusters or DNA nanoballs (DNBs) on a patterned array flow cell.

Another aspect of the invention concerns an apparatus or a sequencing kit for performing the method of the invention, this apparatus or kit comprising (or is consisting of) the following reagents, preferably to be applied upon the MGI platform, and wherein the reagents are present in suitable vials:

a reagent capable of adding nucleotides to the 3-terminus of a single stranded nucleic acid, reagents for a genetic material amplification, preferably reagents for performing a PCR amplification, a reverse transcriptase enzyme, a priming oligonucleotide, possibly a fluorophore, and a template switching motif sequence, which is linked to an at least 6 bases random sequence, preferably between (about) 8 bases and (about) 50 bases, preferably to (about) 12 bases, more preferably the Template Switching Oligonucleotide (TSO) according to the invention.

Advantageously, the apparatus or kit according to the invention may further comprise:

possibly a rolling circle replication enzyme, preferably the Phi 29 DNA polymerase, and one or more of the following elements:

reagents for cyclization, a patterned flow cell, a template independent DNA or RNA polymerase and a blocking nucleotide, such as 3d-NTP, 3-Me-NTP and ddNTP, a system allowing for dual indexing, and possibly (written) instructions for performing the method steps of the invention.

The apparatus according to the invention can be a sequencing device configured to perform a computer-implemented sequencing method of a biological sample under the control of a processor executing instructions, this device comprising a memory device comprising executable application instructions stored therein and a processor configured to execute applications instructions stored in the memory device, these application instructions being able to perform or to control one or more steps of the claimed method of the invention.

In the method, apparatus and kit according to the invention, the priming oligonucleotide preferably comprises the nucleotide sequence disclosed in the claims 9 to 12 and in the claims 19 and 20 of international patent application WO2015/173402, incorporated herein by reference.

Advantageously, in the method, apparatus and kit according to the invention preferably applied upon the MGI platform, the rolling cycle amplification is obtained by addition of a sufficient amount of the Phi 29 DNA polymerase, this polymerase enzyme allows the production of clusters, concatemers or DNA nanoballs (DNBs) into a long single stranded DNA sequence, this sequence comprising several head-to-tail copies of the circular template and wherein the resulting nanoparticle self assembles into a tight ball of DNA. In this embodiment, the polymerase replicates the looped DNA and when it finishes one circle, it does not stop-it, but it continues the replication by peeling off its— previously copied DNA. This copying process continues over and over, thereby forming the DNA cluster or DNA nanoball, as a large mass of repeating DNA to be sequenced all connected together.

Preferably, in the method, apparatus and kit according to the invention the patterned array flow cell is a silicon wafer coated with silicon dioxide, titanium, hexamethyldisilazane (HDMS) and a photoresist material and each DNA nanoball selectively binds to the positively charged amino-silane according to the pattern.

Advantageously, in the preferred method of the invention, the sequencing is obtained by adding dNTP incorporated by polymerase, wherein each dNTP is conjugated to a particular label, preferably a label being a fluorophore or dye and containing a termination blocking addition extension, wherein unincorporated dNTPs are washed, wherein image is captured, wherein dye and terminator are cleaved and wherein these steps are repeated until sequencing is complete. In addition, in the preferred method of the invention, the added fluorophore is excited with a laser that sends light of a specific wavelength, fluorescence emission from each DNA cluster or DNA nanoball is captured on high resolution CCD camera and wherein color of each DNA cluster or each DNA nanoball corresponds to a base to the interrogative position, so that a computer can record a base position information.

A last aspect of the invention concerns the use of the apparatus, the kit or the method according to anyone of the preceding claims, for sequencing or expression analysis, for cloning labelling, for the identification of genes or mutation (s), in personalized medicine, therapy monitoring, prediction, prognosis, early detection of human or animal disease or forensic science, in the analysis of infectious diseases and genomes of viruses, bacteria, fungi, animals or plant, including their derived cells, in the characterization of plants, fruits, breeding checks detection of plants or fruits diseases.

DEFINITIONS

All literature and similar material cited in this application, including, but not limited to, patents, patent applications, scientific articles, books and web pages are expressly incorporated by reference in their entirety to the description of the present invention.

Unless otherwise defined, all terms used in disclosing the invention, including technical and scientific terms, have the meanings as commonly understood by one of ordinary skilled in the art in the invention field.

As used in this specification and claims, the singular forms "a", "an" and "the" include singular or plural referents, unless the content clearly dictates otherwise.

The terms "comprising", "comprises" and "comprised of" are synonymous with "including", "includes" or "containing" and, "contains" are either inclusive or open ended and do not exclude additional, non-recited members, elements or method steps.

The terms "one or more" or "at least one", is clear per se and encompass a reference to any of these members, which means any two or more of the members and up to all members.

The term "about" as used herein, when referring to a measurable value such as an amount of a compound, dose, time and the like is meant to encompass 10%, 9%, 8%, 7%, 6%, 5%, 4%, 3%, 2%, 1%, of the specified amount or value.

As used in the specification and claims, the terms "nucleic acid(s)" comprises polymeric or oligomeric macromolecules, including DNA ((deoxyribonucleic acid) and RNA (ribonucleic acid) known as nucleotides. Comprising bases selected from the group consisting of Adenine (A), Thymine (T), Cytosine (C), Guanine (G) and Uracil (U).

The term "nucleoside" refers to a base linked to ribose cycle by a beta-N9 glycosidic link.

The terms "single stranded nucleic acid" (ss nucleic acid) refer to a nucleic acid, which consist of only one polynucleotide or oligonucleotide strand. In contrast, a "double stranded nucleic acid" (ds nucleic acid) consist of two polynucleotide or oligonucleotide strands wherein the majority of the nucleotides are paired according to known pairing rules.

The term "sample" refers to a part or piece of a tissue, organ or individual, typically being smaller than such tissue, organ or individual, intended to represent the whole of the tissue, organ or individual.

The terms "genetic amplification" is a biochemical technology used in molecular biology for many years to amplify by primers sequences a single or few copies of a piece or portion of DNA by replication and copy across several orders of magnitude, generating thousands to millions of copies of a particular DNA Sequence. The most known genetic amplification technology is the so called "Polymerase Chain Reaction" or PCR, as described in U.S. Pat. No. 4,683,195-B2 and U.S. Pat. No. 4,683,202-B2, using two primers sequences and the heat stable DNA polymerase, such as the Taq polymerase obtained from bacterium *Thermus aquatica* allowing thermal cycling.

The term "primer" refers to a oligonucleotide sequence, usually comprising between about 12 nucleotides and about 25 nucleotides, hybridizing specifically to a target sequence of interest and which functions as a substrate onto which nucleotides can be polymerized by a polymerase.

The terms "Template Switching Oligonucleotide" or "template switch oligo" refer to an oligonucleotide sequence (also referred to as an oligo sequence) that hybridizes to untemplated C nucleotides added by a reverse transcriptase during reverse transcription.

The terms "Template Switching Motif Sequence" correspond to the 3' end of the template switching Oligonucleotide designed to match the overhang nucleotides (that binds to the added bases) by Reverse Transcription during the template switch (by the reverse transcriptase at the 3' end of the cDNA after first strand synthesis as described by M. Matz et al (Nucleic Acids Research, vol 27, No 6 p 1558-1560) (1999)).

The terms "the primer sequence of the Illumina P5 (and P7) adaptor sequence" are known and correspond respectively for single indexing to:

P5:
5' AAT GAT ACG GCG ACC ACC GA 3',
and

P7:
5' CAA GCA GAA GAC GGC ATA CGA GAT 3',
or

P5:
5' AATGATACGGCGACCACCGAGATCTACACGTTCAGAGTTCTACAGT

CCGACGATC 3',
and

P7:
5' GATCGGAAGAGCACACGTCTGAACTCCAGTCAC[i]ATCTCGTATG

CCGTCTTCTGCTTG 3', and for dual indexing to:

P5:
5' AATGATACGGCGACCACCGAGATCTACAC[i5]ACACTCTTTCCCTA

CACGACGCTCTTCCGATCT 3',
and

P7:
5' GATCGGAAGAGCACACGTCTGAACTCCAGTCAC[i7]ATCTCGTATG

CCGTCTTCTGCTTG 3', and refer to amplification primers pairs being a universal primer extension primers pairs as described in the international patent applications WO2007/010251, WO2006/064199, WO2005/065814, WO2015/106941 and WO200/18957, all incorporated herein by reference.

The present invention will be described hereafter in the following examples in reference to the enclosed drawings and presented as non-limiting illustrations of the present invention.

BRIEF DESCRIPTION OF THE DRAWINGS

The enclosed

FIGS. 1 and 2 represent per base sequence quality results in a NextSeq 550 run obtained respectively with the improved CATS construct according to the invention and with the standard CATS construct of the state of the art.

FIGS. 3 and 4 represent per base sequence quality results in a HiSeq 4000 lane (5% phiX) obtained respectively with the standard CATS construct of the state of the art and with the improved CATS construct according to the invention.

EXAMPLES

Figure 1:
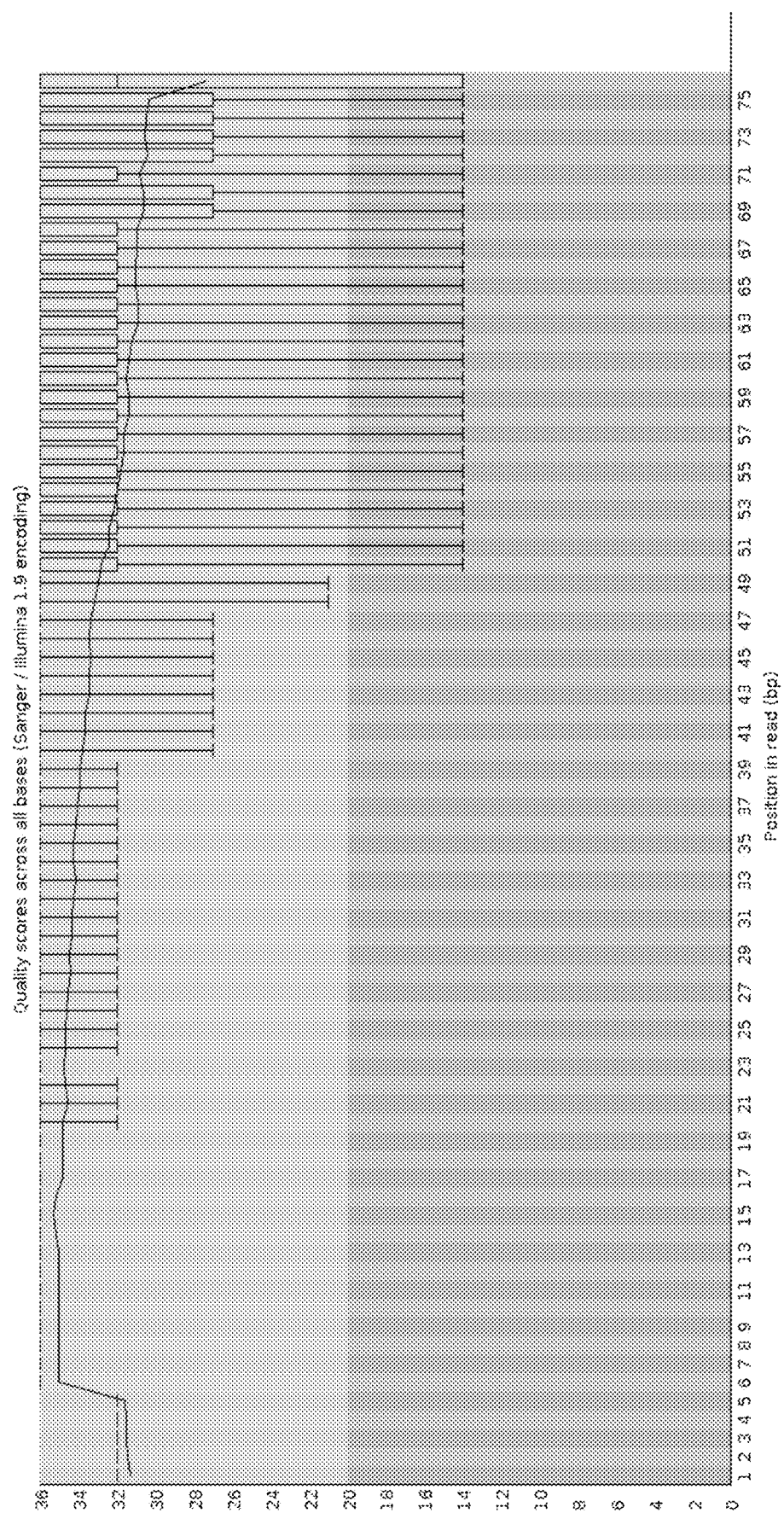
FIGS. 1 to 4 present results of comparative analysis of the quality and quantity of data generated with applied with CATS method of the invention (when the improved CATS construct includes a random sequence) and with CATS method of the state of the art (when the standard CATS construct does not include the random sequence).

Comparative Analysis of the Quality and Quantity of Data Generated from a Sequencing Run Between the CATS-UMI Construct and the Standard CATS Construct

1. Output of the Sequencing Run

The two CATS constructs were sequenced independently on two NextSeq 550 runs. The improved CATS construct, CATS-UMI, was sequenced in a NextSeq 550 HO flow cell in SE50 mode with 3% phiX and following Illumina's recommendations in terms of clusters density. The output of this run is exactly 407 million reads. This is above the maximum (400 million) output described by Illumina in its documentation. Percentage-wise, the output of the run is 101.75%.

On the other hand, the standard CATS construct has been sequenced in a NextSeq 550 MO flow cell in SE50 mode with 20% phiX to prevent any run failure due to the incompatibility of the template switch being read in the first sequencing cycles.

Therefore, it is already logical that the maximum output of the run was never be reached as the library pool has been spiked in to 20%, with an external phiX library, to overcome the low complexity start in the sequencing. Even though, the maximum for this run could only be 80% of the true maximum (taking into account 20% phiX), the run did not even reach that 80% bar.

According to the Illumina protocol, a NextSeq 550 MO (mid-output) run is able to yield maximum 130 million reads. In this situation, this maximum would have to be decreased down to its 80% if it is considered that the clustering of the CATS libraries is going perfectly fine. Thus, the skilled person could expect a maximum output for the pool of CATS libraries to be 104 million of reads. The results of this run was only 94.2 million of reads, meaning 90.58% of what could be have expected at most.

Therefore, sequencing using the standard CATS construct as opposed to the improved CATS-UMI represents two flaws in terms of sequencing output:
a. Using an important phiX spike-in in the library pool thus already decreasing the number of reads a flow cell will generate for CATS libraries;
b. And even though the sequencing run accounts for a significant part of phiX, the space left in output for CATS libraries is not completely filled. This might be also a negative consequence of the CATS clusters beginning with the template switch motif, thus likely hindering the template generation phase of the sequencing.

A confirmation of the better capability of the improved CATS construct (CATS-UMI) according to the invention to generate a higher output has been obtained while comparing the two constructs in a HiSeq 4000 SE50 sequencing, following Illumina's recommendations. The standard CATS construct of the state of the art has been sequenced with 5% phiX while the improved construct was sequenced only with 0.5% phiX for run monitoring purpose.

The difference in output is rather surprising:
Sequencing lane with the standard CATS construct yielded 144 million of reads passing filter out of ~312 million reads (maximum described in Illumina's documentation);
Sequencing lane with the improved construct yielded 314.6 million of reads passing filter out of ~312 million reads (maximum described in Illumina's documentation).

The improved construct is thus able to reach the maximum output and even surpassing it a little bit as in NextSeq sequencing, ~100%, whereas the standard construct is rather working poorly and giving out an output of only 46% of the maximum.

2. Quality of the Sequencing Run

Comparing the 'per base quality' of the two CATS construct depicted in section 1. In a NextSeq run is somehow biased because the standard CATS construct is rescued by a significant spike in of phiX of 20%. Therefore, the 'per base quality' of a CATS library is better thanks to a balanced spike-in such as phiX that is positively impacting the template generation phase among other parameters.

Figure 2:
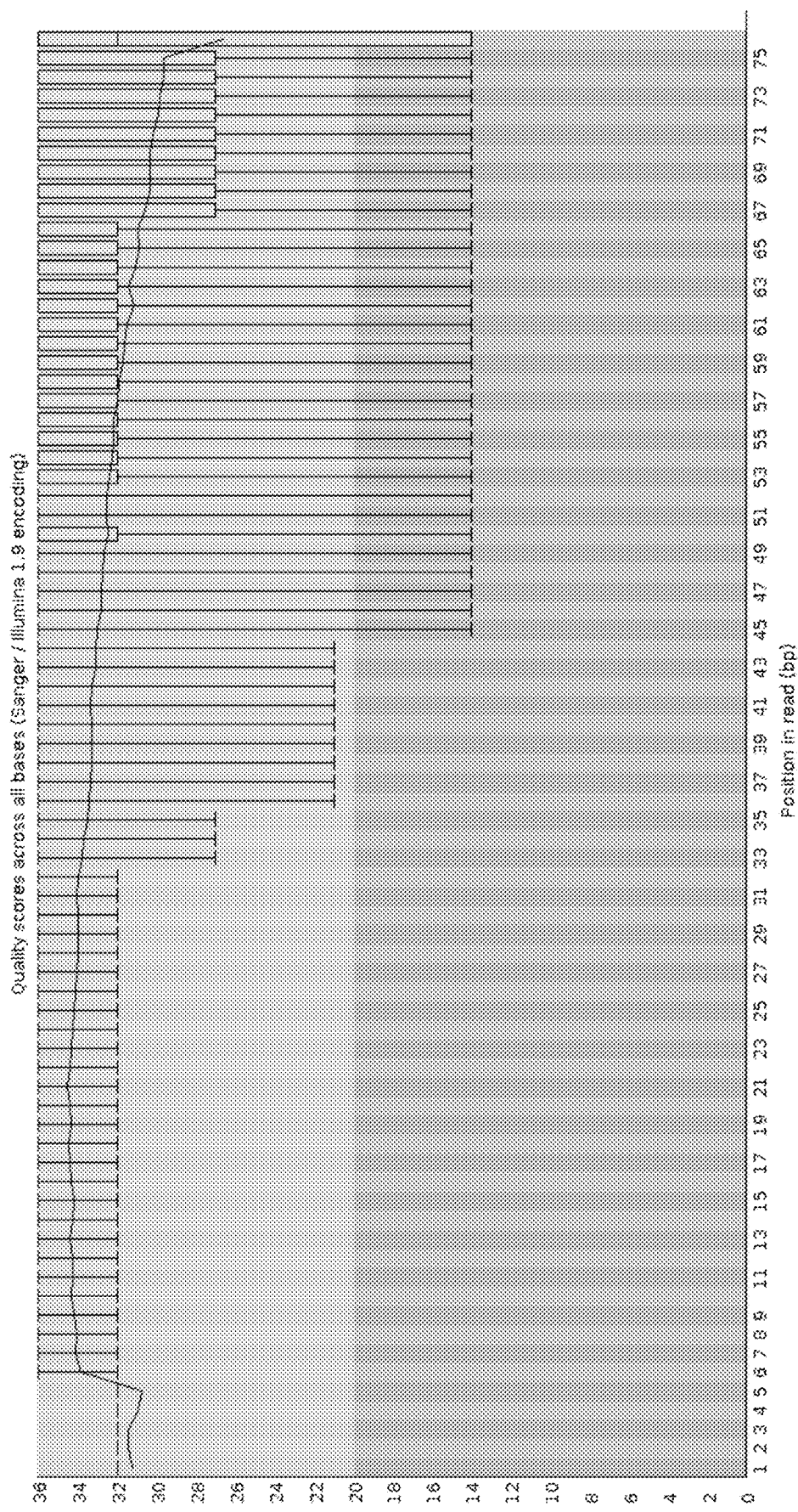

As FIGS. 1 and 2 are showing, the 'per base sequence quality' between the two construct is not obvious. In order to have a better comparison where the phiX spike-in is not playing such a big role, the two constructs have also been sequenced on another Illumina sequencer that is less sensitive to low complexity pattern in the beginning of the read.

The standard CATS construct of the state of the art has been sequenced in a HiSeq 4000 lane with 5% phiX (only) following Illumina's specifications whereas the improved CATS-UMI construct according to the invention has also been sequenced in a HiSeq 4000 lane but with only 0.5% phiX spike-in (for run monitoring purpose).

Figure 3:
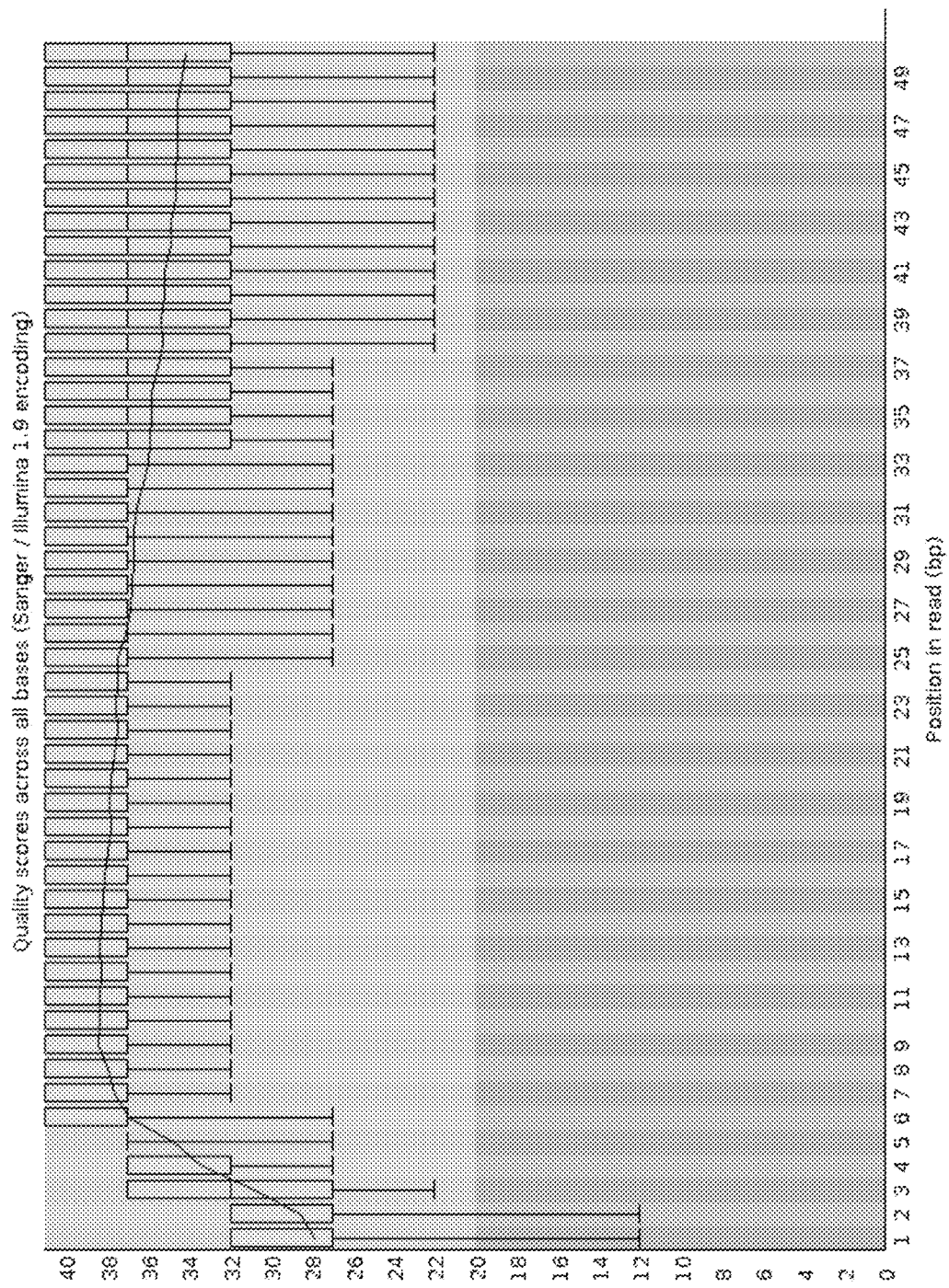
Figure 4:
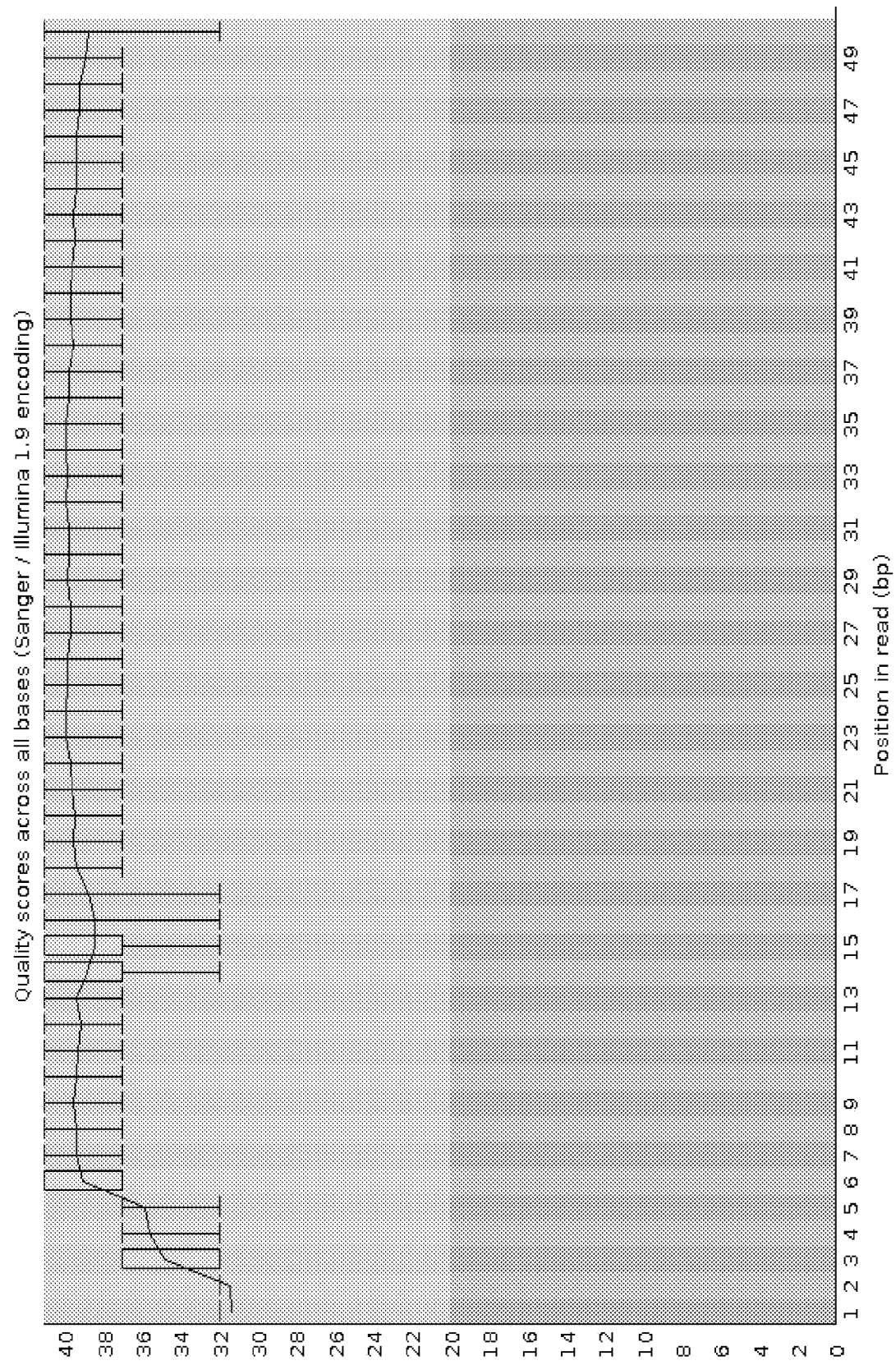

As FIGS. 3 and 4 are showing, the difference in 'per base sequence quality' becomes quite clear. Once the support of the phiX was retrieved from the run, the somehow real 'per base sequence quality' can be observed. When comparing both constructs in FIGS. 3 and 4, the skilled person can easily observe that adding a random sequence before the template switch in the improved CATS construct according to the invention, is highly beneficial in terms of data quality.

3. Conclusion

Based on the results presented herein, the skilled person of the art can observe that the improved CATS construct according to the invention containing a random sequence in front of the template switch motif during read1 is prone to generate more data output from a sequencing run as well as overall better data quality.

---

The invention claimed is:

1. A method of sequencing a nucleic acid sequence, comprising the steps of:
   providing a sample from a single cell, comprising a native single-stranded nucleic acid sequence or native double-stranded nucleic acid sequence in cell-free form,
   adding at least 5 consecutive nucleotides to the 3'-terminus of the native single-stranded sequence, or a fragment thereof, in cell-free form, or to a strand from the native double-stranded nucleic acid sequence, or a fragment thereof, in cell-free form,
   hybridizing a priming oligonucleotide sequence complementary to the added nucleotide sequence and synthesizing a cDNA sequence with a template dependent DNA polymerase to obtain a double-stranded nucleic acid sequence,
   hybridizing to a strand of the generated double-stranded nucleic acid sequence, a template switching oligonucleotide (TSO) comprising a template switching motif sequence, and a random sequence made of at least 6 bases varying among molecules of the TSO, wherein the random sequence is linked to the template switching motif sequence, and wherein the template switching motif sequence hybridizes to overhanging and untemplated C nucleotides added by the template dependent DNA polymerase,
   extending the 3' end of the cDNA sequence to synthesize an extended double-stranded nucleic acid sequence, wherein one strand of the extended double-stranded nucleic acid sequence comprises the priming oligonucleotide and a cDNA sequence that is complementary to the native single-stranded nucleic acid sequence or the fragment thereof, or the strand from the native double-stranded nucleic acid sequence or the fragment thereof, and to the template switching oligonucleotide sequence,
   performing a genetic amplification, and
   performing a base sequencing.

2. The method according to claim 1, wherein the random sequence comprises between 8 bases and 12 bases.

3. The method according to claim 1, wherein the random sequence is composed of more or less equal distribution of bases.

4. The method according to claim 1, wherein the random sequence has a sequence of 12 bases having the sequence NNNNNNNNNNNN or the sequence NNNNBBNNNBBB, wherein B is any nucleotide that comprises a base selected group consisting of Thymidine (T), Guanine (G) or Cytosine (C).

5. The method according to claim 1, wherein the TSO has a length comprised between 29 nucleotides and 48 nucleotides.

6. The method according to claim 1, wherein the TSO is linked by its 5' end to a blocker made of a chemical group.

7. The method according to claim 6, wherein the chemical group is selected from the group consisting of a biotin, a 5'-end abasic site, a 5'-end spacer, and a 5'-end monophosphate.

8. The method according to claim 1, wherein the genetic amplification is performed with a primer sequence complementary to SEQ ID NO:4.

9. The method according to claim 8, wherein the TSO comprises a sequence selected from the group consisting of the sequence SEQ ID NO:1 and the sequence SEQ ID NO:2, wherein the rNrGrGrG is the consensus Template Switch Motif sequence, rN is a nucleoside or any ribonucleotide of a RNA sequence and rG is a ribonucleotide of the base Guanine (G).

10. The method according to claim 1, wherein the TSO consists of the sequence SEQ ID NO:3, wherein rNrGrGrG is the consensus Template Switch Motif sequence, rN is a nucleoside or any ribonucleotide of a RNA sequence and rG is a ribonucleotide of the base Guanine (G).

11. The method according to claim 1, wherein the at least 5 consecutive identical nucleotides are selected from the group consisting of ribonucleotides, deoxy-ribonucleotides or dideoxy-ribonucleotides of A, T, C, G or U.

12. The method according to claim 1, wherein the template switching motif sequence linked to the random sequence is provided in a Template Switching Oligonucleotide construct having from a 5' end towards a 3' oriented end:
  a primer sequence; and
  the template switching motif sequence which is linked to the said primer sequence by the random sequence of at least 6 bases.

13. The method according to claim 1, wherein the sequencing is obtained by adding dNTPs incorporated by a polymerase, each dNTP being conjugated to a label and containing an extension terminator, wherein unincorporated dNTPs are washed, wherein image is captured, wherein dye and terminator are cleaved and wherein these steps are repeated until sequencing is complete.

14. The method of claim 13, wherein the label is a fluorophore and the fluorophore is excited with a laser that emits light of a specific wavelength.

15. The method of claim 14, wherein fluorescence emission from each DNA cluster is captured on high resolution CCD camera, wherein a color of each detected DNA cluster corresponds to the interrogative position and wherein a computer records base position information.

16. The method according to claim 1, wherein the native single-stranded nucleic acid sequence or native double-stranded nucleic acid sequence is selected from the group consisting of fragmented and/or bisulfite-converted DNA sequence, mRNA sequence, miRNA sequence, small RNA sequence, piRNA sequence, bisulfite-converted RNA and a mixture thereof.

17. The method according to claim 1 further comprising one or more of the additional steps of:
  denaturing the native double strand nucleic acid sequence,
  fragmenting the native single-stranded nucleic acid sequence or the native double-stranded nucleic acid sequence into smaller nucleic acid sequence fragments, and
  end-repairing the native single-stranded sequence or the native double-stranded nucleic acid sequence.

* * * * *